US010053718B2

United States Patent
Saxena et al.

(10) Patent No.: US 10,053,718 B2
(45) Date of Patent: Aug. 21, 2018

(54) ISOLATED BACTERIAL STRAIN OF GLUCONACETOBACTER OBOEDIENS AND AN OPTIMIZED ECONOMIC PROCESS FOR MICROBIAL CELLULOSE PRODUCTION THEREFROM

(71) Applicant: Council of Scientific & Industrial Research, New Delhi (IN)

(72) Inventors: Rajendra Kumar Saxena, New Delhi (IN); Firdaus Jahan, New Delhi (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 509 days.

(21) Appl. No.: 13/967,985

(22) Filed: Aug. 15, 2013

(65) Prior Publication Data

US 2014/0080184 A1    Mar. 20, 2014

Related U.S. Application Data

(63) Continuation-in-part of application No. PCT/IB2012/050679, filed on Feb. 15, 2012.

(30) Foreign Application Priority Data

Feb. 15, 2011    (IN) ............... 0389/DEL/2011

(51) Int. Cl.
*C12N 1/20* (2006.01)
*C12P 19/04* (2006.01)
*C12R 1/02* (2006.01)

(52) U.S. Cl.
CPC .......... *C12P 19/04* (2013.01); *C12N 1/20* (2013.01); *C12R 1/02* (2013.01)

(58) Field of Classification Search
None
See application file for complete search history.

(56) References Cited

U.S. PATENT DOCUMENTS 7,709,631 B2    5/2010    Harris et al.

FOREIGN PATENT DOCUMENTS

WO    2012/110960    8/2012

OTHER PUBLICATIONS

Kim et al. "Production of Bacterial Cellulose by *Gluconacetobacter* sp. RKY5 isolated from Persimmon Vinegar" Applied Biochemistry and Biotechnology, vol. 129-132, 2006.*

(Continued)

*Primary Examiner* — Blaine Lankford
*Assistant Examiner* — Lauren K Van Buren
(74) *Attorney, Agent, or Firm* — Westman, Champlin & Koehler, P.A.

(57) ABSTRACT

The present invention provides a novel and potent cellulose producing bacterial species, *Gluconacetobacter oboediens* which was isolated from mixed fruit residue deposited at MTCC, IMTECH, Chandigarh under the deposition number MTCC 5610. The process for the production of microbial cellulose by this bacterium was optimized and thus, an efficient and economic process for producing high titers of microbial cellulose was developed. Further, a novel and improved method for drying of microbial cellulose has been developed wherein the microbial cellulose mats were dried using a wooden plank and porous fabric as a base at room temperature. The microbial cellulose production was successfully scaled up to 5 liters volume of production medium in trays. The present invention also recites the production and optimization of microbial cellulose in different shapes and sizes (gloves and vessels) which will be of great help for burn and injured persons/patients.

5 Claims, 7 Drawing Sheets

A. Bacteria producing cellulose fibrils

B. Ultrafine cellulose fibrils

Scanning Electron Micrograph (SEM) of the microbial cellulose

(56) References Cited

OTHER PUBLICATIONS

Kim Soo-Yeon et al. "Production of bacterial cellulose by *Gluconacetobacter* sp RKY5 isolated from persimmon vinegar," Applied Biochemistry and Biotechnology, vol. 131, No. 1-3, Mar. 2006 (Mar. 2006), pp. 705-715, XP002681688, ISSN: 0273-2289, the whole document.*
Tang Wei-Hui et al. "Screening and fermenation conditions of strains from Gluconacetobacter oboediens for high-yield bacterial cellulose production," Modern Food Science and Technology 2009 Key Lab of Ind. Microbiol, Min. of Education, Tianjin Univeristy. of Sci & Tech, Tianjin 300457, China, vol. 25, No. 9, 2009, p. 1016, abstract.*
Wee et al. "Isolation and characterization of a bacterial cellulose producing bacterium derived from the persimmon vinegar." African Journal of Biotechnology vol. 10(72), pp. 16267-16276.*
Kim Soo-Yeon et al.: "Production of bacterial cellulose by *Gluconacetobacter* sp RKY5 isolated from persimmon vinegar", Applied Biochemistry and Biotechnology, vol. 131, No. 1-3, Mar. 2006 (Mar. 2006), pp. 705-715, XP002681688, ISSN: 0273-2289, the whole document.
Park Joong Kon et al.: "Production of bacterial cellulose by Glucenacetobacter hasenii PJK isolated from rotten apple.", Biotechnology and Bioprocess Engineering, vol. 8, No. 2, Mar. 2003 (Mar. 2003), pp. 83-88, XP002681689, ISSN: 1226-8372, the whole document.
Tang Wei-Hua et al.: "Screening and fermentation conditions of strains from Gluconacetobacter oboediens for high-yield bacterial cellulose production.", Modern Food Science and Technology 2009 Key Lab. of Ind. Microbiol., Min. of Education, Tianjin Univ. of Sci. & Tech., Tianjin 300457, China, vol. 25, No. 9, 2009, p. 1016, XP008154705, abstract.
Bae Sangok et al.: "Statistical optimization of culture conditions for bacterial cellulose production using Box-Behnken design", Biotechnology and Bioengineering, vol. 90, No. 1, Apr. 2005 (Apr. 2005), pp. 20-28, XP002681690, ISSN: 0006-3592, the whole document.
Y Andelib Aydin and Nuran Deveci Askoy: "Isolation of cellulose producing bacteria from wastes of vinegar fermentation", Proceedings of the World Congress on Engineering and Computer Science (October 20-22, 2009, San Francisco, USA), vol. 1, 2009, pp. 1-4, XP002681691, ISBN: 978-988-17012-6-8, the whole document.
Lisdiyanti Puspita et al.: "Reclassification of Gluconacetobacter hansenii strains and proposals of *Gluconacetobacter saccharivorans* sp nov and *Gluconacetobacter nataicola* sp nov.", International Journal of Systematic and Evolutionary Microbiology, vol. 56, No. Part 9, Sep. 2006 (Sep. 2006), pp. 2101-2111, SP002681692, ISSN: 1466-5026, the whole document.
Firdaus Jahan et al.: "Production of Microbial Cellulose by a Bacterium Isolated from Fruit", Applied Biochemistry and Biotechnology; Part A: Enzyme Engineering and Biotechnology, Humana Press Inc., New York, vol. 167, No. 5, Mar. 7, 2012 (Mar. 7, 2012), pp. 1157-1171, XP035087977, ISSN: 1559-0291, DOI: 10.1007/S12010-012-9595-X, the whole document.
International Search Report and Written Opinion for PCT Application No. PCT/IB2012/050679, dated Aug. 22, 2012, 15 pages.
International Preliminary Report on Patentability for PCT Application No. PCT/IB2012/050679, dated May 8, 2013, 9 pages.
Article 34 Response for PCT Application No. PCT/IB2012/050679, dated Dec. 17, 2012, 13 pages.
Written Opinion of the International Preliminary Examining Authority for PCT Application No. PCT/IB2012/050679, dated Feb. 14, 2013, 9 pages.
Response to Written Opinion of the International Preliminary Examining Authority for PCT Application No. PCT/IB2012/050679, dated May 14, 2013, 14 pages.

\* cited by examiner

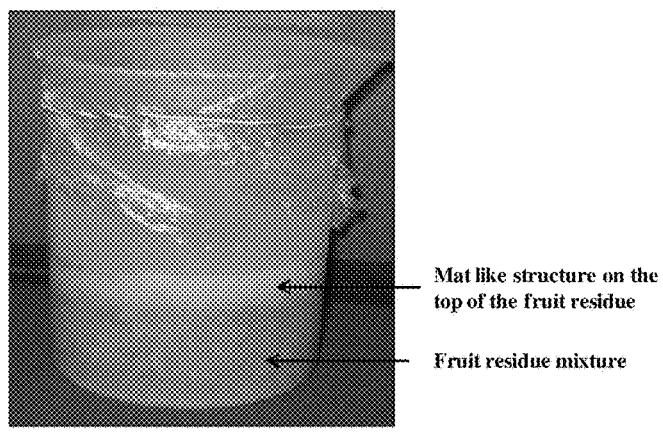
Fig. 1: Formation of a mat like structure( microbial cellulose) on the surface of fruits residue

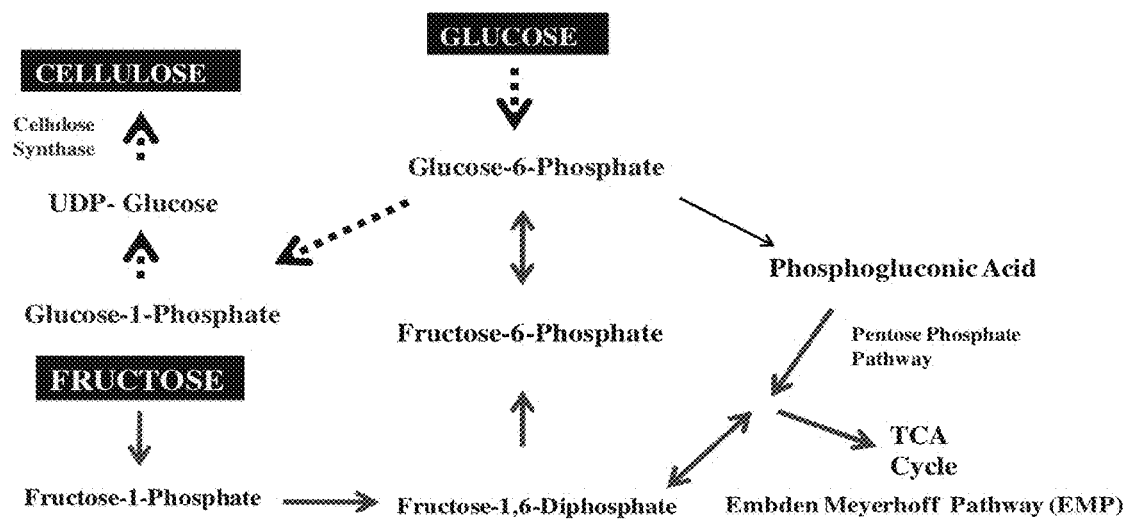
Fig. 2: Microbial cellulose production pathway

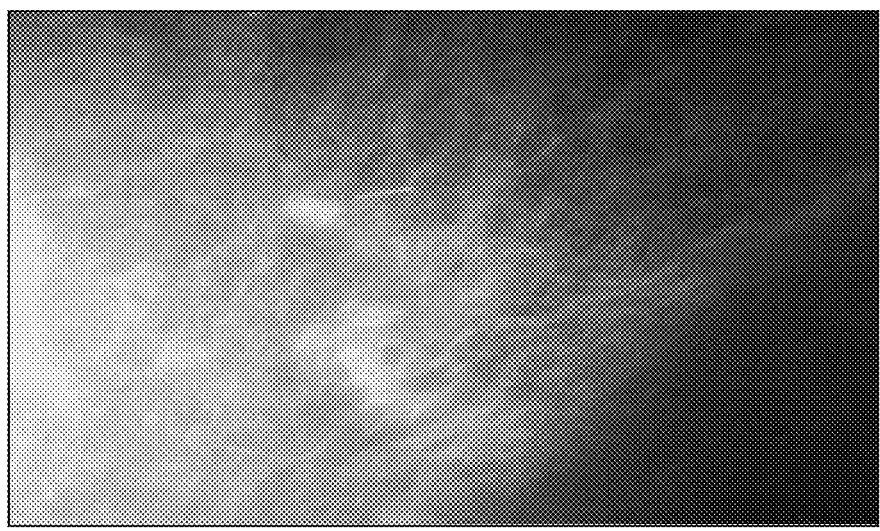
Fig. 3: Observation of microbial cellulose under epifluorescent microscope after staining with calcofluor white stain

 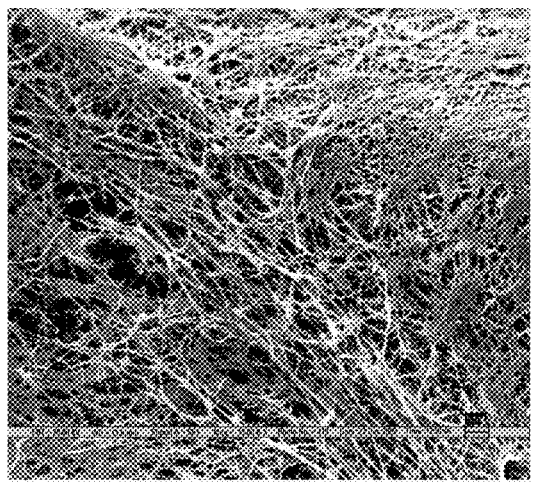
A. Bacteria producing cellulose fibrils        B. Ultrafine cellulose fibrils
Fig. 4: Scanning Electron Micrograph (SEM) of the microbial cellulose

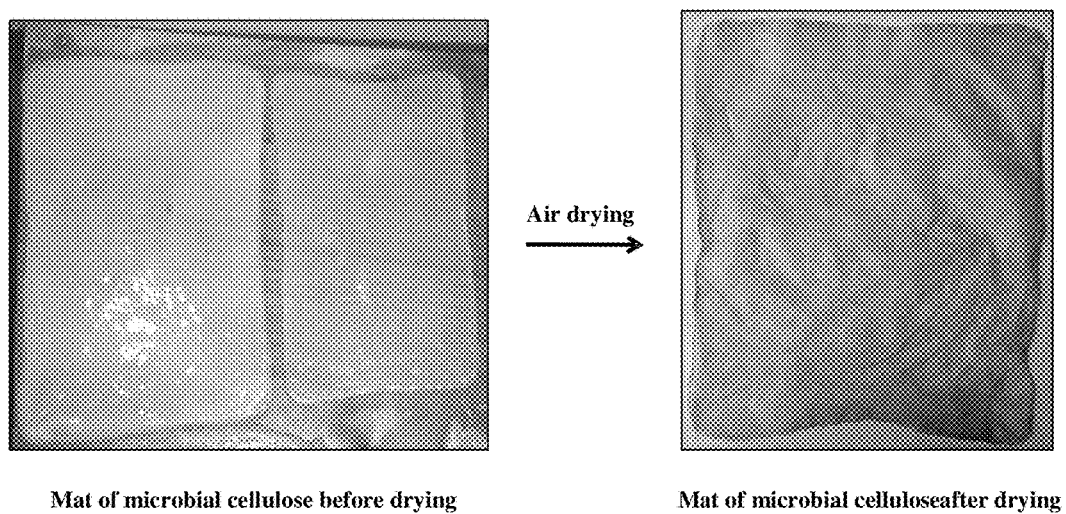
Fig. 5: Drying process of microbial cellulose at room temperature (air drying) on wooden plank

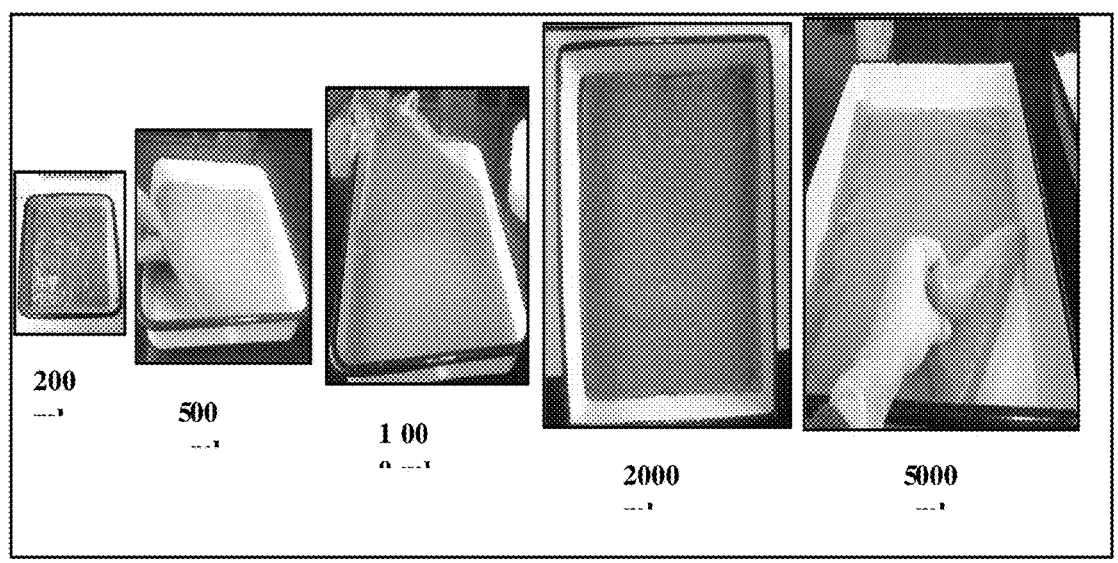
Fig. 6: Scale up of microbial cellulose production in trays

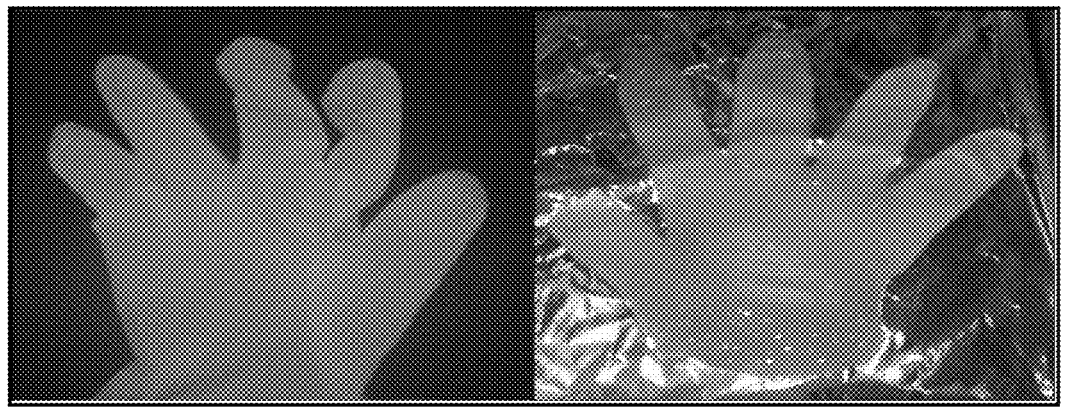
Latex glove    Microbial cellulose in the shape of glove
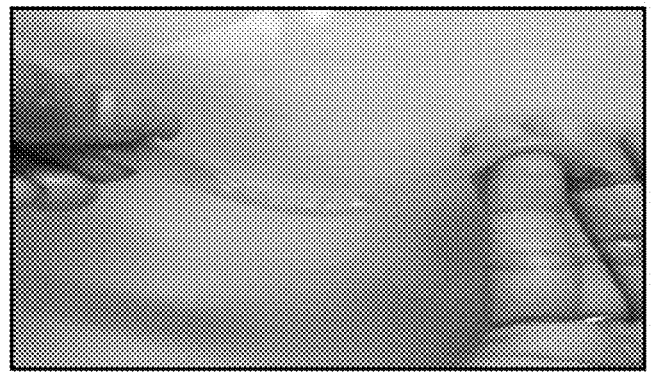
Microbial cellulose in the shape of a vessel
Fig. 7: Production of microbial cellulose in different shapes (eg. gloves and vessels)

SEQUENCE LISTING

```
<160> NUMBER OF SEQ ID NOS: 1

<210> SEQ ID NO 1
<211> LENGTH: 890
<212> TYPE: DNA
<213> ORGANISM: Gluconacetobacter oboediens

<400> SEQUENCE: 1
tttttttccc ccccggaacg tcacgcggca tcctgatccg cgattactag cgattccacc     60
ttcatgcact cgagttgcag agtgcaatcc gaactgagac ggcttttga gatcggctcg    120 gtgtcaccac ctggcttccc actgtcaccg ccattgtagc acgtgtgtag cccaggacat    180
aagggccatg aggacttgac gtcatcccca ccttcctccg gcttgtcacc ggcagttcct    240
ttagagtgcc cacccagacg tgatggcaac taaaggcgag ggttgcgctc gttgcgggac    300
ttaacccaac atctcacgac acgagctgac gacagccatg cagcacctgt gctggaggtc    360
tcttgcgaga aatgcccatc tctggacacg gcctccgcat gtcaagccct ggtaaggttc    420
tgcgcgttgc ttcgaattaa accacatgct ccaccgcttg tgcgggcccc cgtcaattcc    480
tttgagtttc aaccttgcgg ccgtactccc caggcggtgt gcttatcgcg ttaactacga    540
cactgaatga caaagtcacc caacatccag cacacatcgt ttacagcgtg gactaccagg    600
gtatctaatc ctgtttgctc cccacgcttt cgcgcctcag cgtcagtcat gagccaggtt    660
gccgccttcg ccaccggtgt tcttcccaat atctacgaat ttcacctcta cactgggaat    720
tccacaaccc tctctcacac tctagtcgcc acgtatcaaa tgcagccccc aggttaagcc    780
```

```
cgggaatttc acatctgact gtgtcaaccg cctacgcgcc ctttacgccc agtcattccg      840
agcaacgctt gccccttcg tactacagcg ctgcgcgcgc gcacacaaag                  890
```

ISOLATED BACTERIAL STRAIN OF GLUCONACETOBACTER OBOEDIENS AND AN OPTIMIZED ECONOMIC PROCESS FOR MICROBIAL CELLULOSE PRODUCTION THEREFROM

CROSS-REFERENCE TO RELATED APPLICATIONS

The present application is a continuation in part of and claims priority of International patent application Serial No. PCT/IB2012/050679, filed Feb. 15, 2012, and published in English as WO2012/110960, which claims priority of Indian patent application 0389/DEL/2011, filed Feb. 15, 2011. The contents of these applications are hereby incorporated by reference in their entirety.

FIELD OF THE INVENTION

The present invention relates to a novel isolated bacterial strain of *Gluconacetobacter oboediens* and an optimized economic process for microbial cellulose production therefrom. In particular, the present invention relates to a low cost optimized process for microbial cellulose production under static culture conditions by a new bacterial species *Gluconacetobacter oboediens* MTCC 5610 isolated from fruit residues. More particularly, the present invention relates to the isolation of a novel, potent cellulose producing bacterial species from fruit residues and the development of an economic process for the production of microbial cellulose in any amount, size, shape and dimension and further provides the drying methods therefor.

The main exploitation of microbial cellulose is in the medical field where it can be used as wound dressings or bandages, artificial skin, for making artificial vessels and other biomedical devices. Besides this, microbial cellulose can also be used in many other industrial sectors like cosmetics, paper, textile, food, environmental remediation and also in manufacturing of many products like audio diaphragms, baby care products, sports goods etc.

BACKGROUND OF THE INVENTION AND DESCRIPTION OF PRIOR ART

Cellulose in General (Plant)

Cellulose is the most abundant biological macromolecule on the planet earth. It forms the basic structural matrix of the cell walls of nearly all plants, many fungi and some algae. It is a major biopolymer of tremendous economic importance as it find multifarious uses in industries such as textiles, pulp and paper, cosmetics, healthcare, food, audio products, sport goods, etc, as well as in the preparation of cellulose derivatives such as cellophane, rayon, cellulose acetate and few others. Apart from this, cellulose is also used for environmental remediation especially in treating oil spills and removing toxic materials. The demand for cellulose has traditionally been met by wood and cotton, which contain over 50% and over 94% cellulose, respectively. However, plant resources cannot sustain an increasing demand for cellulose requirements due to fast diminishing forest resources, decreased land holdings for agriculture and other environmental concerns. This along with the difficulty in removal of hemicellulose or lignin inherently associated with cellulose limits its applications. It, therefore, necessitates a search for a commercially viable alternative to plant cellulose.

Microbial Cellulose as an Alternative to Plant Cellulose and its Importance

Microbial cellulose has emerged as an important and viable alternative to plant cellulose. Since ages, cellulose is recognized as the major component of plant biomass. However, it also represents a major chunk of microbial extracellular polymers. The cellulose produced by microbes is called microbial cellulose (MC). It is an exopolysaccharide. Some bacteria are in condition to produce cellulose, as reported from the strains of the genera *Gluconacetobacter* (formerly *Acetobacter*), *Agrobacterium*, *Pseudomonas*, *Rhizobium* and *Sarcina*.

The production of cellulose by *Acetobacter xylinum* was reported for the first time in 1886 by A. J. Brown. He observed that the resting cells of *Acetobacter* produced cellulose in the presence of oxygen and glucose. This non-photosynthetic organism can procure glucose, glycerol, or other organic substrates and can convert them into pure cellulose. *A. xylinum* was reported as the most efficient producer of MC. The production of cellulose can be carried out in either solid-phase cultivation or submerged culture. Investigations have been focused on the mechanism of biopolymer synthesis, as well as on its structure and properties, which determine practical use thereof (Legge, 1990; Ross et al., 1991). *Acetobacter xylinum* produces two forms of cellulose: Cellulose I, the ribbon like polymer, and Cellulose II, the thermodynamically more stable amorphous polymer. Plant and bacterial cellulose are chemically the same, $\beta$ 1, 4 glucans, having same molecular formula $(C_6H_{10}O_6)_n$ but their physical features are different (Yoshinaga et al., 1997). As compared to plant cellulose, bacterial cellulose is chemically purer, has a high degree of crystallinity, polymerization, tensile strength, shear resistance and high water holding capacity. Fibrils of bacterial cellulose are about 100 times thinner than that of plant cellulose, making it more porous material.

Research on microbial cellulose production has been sporadically attempted with an increased impetus after 1990s. Production of microbial cellulose was carried out either in static or shaking culture. Glucose is supposed to be the most common carbon source for microbial cellulose production. However, there are many reports of microbial cellulose production using other carbon sources. In a study by Oikawa et al (1995) microbial cellulose production is carried out using D-Arabitol by *Acetobacter xylinum*. Similarly, Yang et al (1998) carried out the production of microbial cellulose by *Acetobacter xylinum* under shaking conditions using glucose, fructose, and sucrose individually and in combination. Microbial cellulose production by *Acetobacter xylinum* has been also attempted using D-xylose as a carbon source by Ishihara et al (2002). Keshk and Sameshima (2005) evaluated the effect of different carbon sources on the production of bacterial cellulose by *Acetobacter xylinum* and found that glycerol gave the highest yield of bacterial cellulose. In 2008, Hong and Qiu, developed a new carbon source from konjac powder that enhanced production of bacterial cellulose by *A. aceti* subsp. *xylinus* in static cultures.

Optimization studies on the production of microbial cellulose can enhance the yield both in static and shaking condition. Many scientists have attempted to optimize the culture conditions in order to enhance microbial cellulose production. In 2002, Heo and Son developed an optimized, simple and chemically defined medium for bacterial cellulose production by *Acetobacter* sp. V9 in shaking culture. In 2005, Bae and Shoda, statistically optimized the culture conditions for the bacterial cellulose production in shaking condition by *Acetobacter xylinum* using response surface methodology. Kim et al (2006) developed an optimized medium for the production of microbial cellulose in static condition by *Glucanocetobacter* sp. isolated from persimmon vinegar. An optimized medium for microbial cellulose production in static condition by *Acetobacter* sp. 4 B-2 was developed by Pourramezan et al., (2009), who studied the bacterial cellulose production using two categories of carbon sources (monosaccharides and disaccharides) and found sucrose to be the best carbon source for cellulose production. Jung et al., (2010) used a cost effective molasses-corn steep liquor medium for microbial cellulose production under shaking culture conditions by *Acetobacter* sp. V6.

Microbial cellulose yield in static cultures is mostly dependent on the surface/volume ratio. Microbial cellulose synthesis in static conditions can be achieved either in a one step [as attempted by most of the workers] or a two-step procedure using agitated fermentation followed by the static culture (Okiyama et al., 1992). They also scaled up the production upto 800 ml.

Attempts to produce microbial cellulose using conventional fermentors in order to scale up production in agitated condition have yielded few significant results. Bungay and Serafica (U.S. Pat. No. 6,071,727, 2000) worked on the production of microbial cellulose using a rotating disc or linear conveyer bioreactor. Chao et al (2000) used an airlift reactor for the production of microbial cellulose by *Acetobacter xylinum*. Tung et al (1997) modified the airlift reactor to improve the performance of fermentation processes. The production of microbial cellulose by *Acetobacter xylinum* was carried out in a jar fermentor and the effect of the pH and dissolved oxygen on production was observed (Hwang et al., 1999). In 2005, Bae and Shoda produced bacterial cellulose by *Acetobacter xylinum* subsp. *sucrofermentans* using molasses medium in a jar fermentor.

Microbial cellulose can be dried either by freeze drying, air drying, vacuum oven drying or drying in a simple oven. Most of the workers have dried microbial cellulose in a vacuum oven (Chao et al., 2000, Bae and Shoda, 2005, Kim et al., 2006 and Pourramezan et al., 2009). The purified bacterial cellulose pellets were dried to a constant weight at 80 to 105 degree C. in a conventional oven (Hwang et al., 1999 and Son et al., 2001). Harris et al., 2010 (U.S. Pat. No. 7,709,631 B2), have air dried the microbial cellulose mats at 37° C. using polypropylene mesh as base for drying.

Reference may be made to the study of Kim et al (2006) which utilizes a bacterial strain *Gluconacetobacter* sp. RKY5 for cellulose production. The strain was isolated from persimmon vinegar as opposed to the strain of *Gluconacetobacter oboediens* isolated in the present invention from fruits residue. Also, the bacterial strain *Gluconacetobacter oboediens* is novel cellulose producing bacterial strain and has not been yet reported to produce cellulose. This is the first report of cellulose production by *Gluconacetobacter oboediens* and that too with much higher yield. The higher microbial cellulose yield by the bacterium of the present invention can be explained on the fact that *Gluconacetobacter oboediens* MTCC 5610 is more potent than the strain of Kim et al (2006). Also, the difference in the final yields of microbial cellulose in the present study and the study of Kim et al lies in the method of process optimization. After process optimization w.r.t. different parameters by "one variable at time approach" and then, "Response Surface Methodology", (statistical optimization), the inventors of the present invention achieved a maximum microbial cellulose production of 11.8 g/L, which can be further increased by auxiliary optimization experiments. However, it may be noted that Kim et al (2006), have optimized the process parameters by only "one variable at a time approach" and no statistical optimization was carried out in their study. Further, the process of the present invention is more economic and simple for microbial cellulose production as compared to their process.

Consequently, by all the facts reported above it can be concluded that the bacterial strain *Gluconacetobacter oboediens* MTCC 5610 is different from the strains reported in the prior art for microbial cellulose production. Further, the process optimization for achieving higher yields was more efficient and economic than that carried out by the earlier studies.

In summary, the drawbacks of the hitherto reported literature can be summarized as follows:

There are only few reports on the microbial cellulose production by newer species of *Acetobacter* (*Gluconacetobacter*) and other bacterial strains. Most of the work on microbial cellulose has been carried out using *Acetobacter xylinum*, which is the most common and well known cellulose producer.

Most of the researches have been conducted only upto flask level, (i.e 30 or 50 ml production medium in a 250 ml Erlenmeyer flask) and a calculated yield per liter is presented. These results do not clearly explain the scalability of the production.

There are few reports of microbial cellulose production in static culture condition providing significant titers. There is no report directly related to the scale up of microbial cellulose production in static culture. Most of the workers have scaled up the production in agitated culture either in a jar fermentor or airlift fermentor. Static culture is important as it produces microbial cellulose in a sheet or mat form which is essential for some important applications of microbial cellulose especially in the medical field as wound dressings, artificial skin substitute, material for arterial implants and others.

Detailed description on the drying method and recovery of the microbial cellulose therefrom has not been presented by any of the workers. Drying step is very important as it gives the final dry weight i.e final yield of the microbial cellulose produced. There is only one patent by Harris et al., 2010 (U.S. Pat. No. 7,709,631 B2) which has explained the air drying process of microbial cellulose, wherein they have kept the microbial cellulose mats between two pieces of polypropylene mesh and further, kept them in an incubator at 37° C. for 18-36 h. However, the use of polypropylene mesh and incubator thereby for drying is less economical as compared to the process used in the present invention i.e. drying on a wooden plank and a porous fabric which is quite economical.

Objects of the Invention

The main object of the present invention is therefore to provide a novel isolated bacterial strain of *Gluconacetobacter oboediens* MTCC 5610 isolated from fruit residues, which is capable of producing appreciable amounts of microbial cellulose.

Another object of the present invention is to provide an optimized process for large scale production of microbial cellulose in static culture which is economically viable and cost effective.

Still another object of the present invention is to obtain high microbial cellulose yield using cheap agro wastes.

Yet another object of the present invention is to provide a novel method for the efficient drying of the microbial cellulose.

Still another object of the present invention is to scale up the production of microbial cellulose upto any amount and size under static culture conditions.

SUMMARY OF THE INVENTION

The present invention provides a novel and potent cellulose producing bacterial species, *Gluconacetobacter oboediens* isolated from fruit residue (this bacterial culture has been deposited at MTCC, IMTECH, Chandigarh under the deposition number MTCC 5610). The production of microbial cellulose by this bacterium was process optimized and thus, an efficient and economic process for producing high tires of microbial cellulose was developed. Further, a novel and improved method for drying of microbial cellulose was developed wherein the microbial cellulose mats were dried using a wooden plank and porous fabric as a base at temperature of 30 to 40 degree C. The microbial cellulose production was successfully scaled upto 5 liters volume of production medium in trays. The present invention also involves the production and optimization of microbial cellulose in different shapes and sizes (gloves and vessels) which will be of great help for curing burn and injured persons/patients.

Thus, the present invention provides an optimized economic process for the production of microbial cellulose in static conditions from a new bacterial species, *Gluconacetobacter oboediens*. The microbial cellulose producing bacterial species was isolated from mixed fruit residues obtained from local market of Satya Niketan, New Delhi—110021, India. The fruit residue was mixed with sugar and water in the ratio of 1 to 3:0.1 to 0.5:2 to 4 respectively followed by incubating for 10 to 15 days at 25 to 35 degree C. in a wide mouthed plastic container so as to isolate the microbial cellulose producers.

Accordingly, the present invention provides a novel isolated bacterial strain of *Gluconacetobacter oboediens* having accession number MTCC 5610, wherein the said strain being deposited at the Microbial Type Culture Collection, MTCC, Chandigarh, India a depository recognized under the Budapest Treaty.

The deposited material has been accepted for deposit under the Budapest Treaty of the International Recognition of the Deposit of Microorganisms and all restrictions on the availability to the public of the material so deposited will be irrevocably removed upon the granting of a patent. The deposit is identified by *Gluconacetobacter oboediens* MTCC 5610, on Mar. 31, 2011, at Microbial Type Culture Collection & Gene Bank, Institute of Microbial Technology, Sector 39-A, Chandigarh, 160036, India.

The invention further provides an optimized economic process for the production of microbial cellulose using the isolated bacterial strain MTCC 5610, wherein the said process comprising the following steps:

a) growing the bacterial isolate of *Gluconacetobacter oboediens* MTCC 5610 under aerobic and static culture conditions in the production medium having 0.1 to 20.0% of a carbon source; 0.5 to 8.0% of a nitrogen source; 0.1 to 0.5% of salts for 4 to 15 days; wherein the pH during cultivation is in the range of 3.0 to 12.0 and the temperature ranges from 10 to 45 degree C.;

b) recovering the microbial cellulose mat from the medium of step [a], followed by drying at a temperature of 10 to 45 degree C. for 40 to 45 hours.

In an embodiment of the invention, the microbial cellulose was produced by growing *Gluconacetobacter oboediens* under aerobic conditions in the production medium with pH value ranging from 3.0 to 12.0 containing carbon and nitrogen sources in the range from 0.1 to 20.0% and 0.5 to 8.0% respectively, wherein the temperature during cultivation was maintained in the range of 10 to 45 degree C.

In another embodiment of the invention, the carbon source used is very economic; preferably commercially available table sugar.

In yet another embodiment, the nitrogen source used for the production of microbial cellulose may be a a cheap agro waste.

The present invention further relates to a process for drying of the microbial cellulose, scale up of the production in trays and production of microbial cellulose in different shapes.

In an embodiment, the present invention provides a novel process for the drying of microbial cellulose at 30 to 40 degree C.

In another embodiment of the invention, the scale up of the microbial cellulose production was carried out in different tray sizes upto 5 liters.

In yet another embodiment of the invention, a wooden plank and a porous fabric was used for drying of the microbial cellulose.

In still another embodiment, the microbial cellulose was produced in the shape of gloves and vessels.

BRIEF DESCRIPTION OF THE ACCOMPANYING DRAWINGS

In the drawings accompanying the specification, FIG. 1 reveals the formation of a mat like structure (microbial cellulose) on the surface of the fruits residue.

In the drawings accompanying the specification, FIG. 2 shows the mechanism of cellulose biosynthesis.

In the drawings accompanying the specification, FIG. 3 shows the picture of microbial cellulose observed under epifluorescent microscope after staining with calcofluor white stain.

In the drawings accompanying the specification, FIG. 4 shows the scanning electron micrograph of the microbial cellulose.

In the drawings accompanying the specification, FIG. 5 illustrates the drying process of microbial cellulose at temperature of 30 to 40 degree C. on a wooden plank.

In the drawings accompanying the specification, FIG. 6 reveals the scale up process of microbial cellulose production in trays.

In the drawings accompanying the specification, FIG. 7 shows the production of microbial cellulose in different shapes (eg. gloves and vessels).

DETAILED DESCRIPTION OF THE INVENTION

The present invention provides a process for the isolation of microbial cellulose producing novel bacterial strains isolated from mixed fruit residues. The mixed fruit residue used in the present invention for the isolation of cellulose producing bacteria was collected from a local market of Satya Niketan, New Delhi—110021, India. Of the several isolated strains the novel bacterial strain of *Gluconacetobacter oboediens* was selected for further studies as it was found to be the most potent microbial cellulose producer. This strain was deposited at the Microbial Type Culture Collection, MTCC, Chandigarh, India a depository recognized under the Budapest Treaty and has been accorded the deposit number MTCC 5610.

The detailed morphological, cultural and biochemical characteristics of the isolated strain of *Gluconacetobacter oboediens* MTCC 5610 are as follows:

| Tests | Characteristics |
|---|---|
| Growth on agar medium | Small, circular and rough colonies; Pellicle-forming colonies in presence of glucose |
| Growth in liquid medium | Not uniform |
| Colour | Off-white to cream |
| Pigment production | No |
| Gram reaction | Negative |
| Morphology | Rod shaped |
| Arrangement | Singly, in pairs or in short chain |
| Sporulation | No |
| Motility | Motile |
| Growth on 3% ethanol in the presence of 5-8% acetic acid | + |
| Growth at a glucose concentration of 30% (w/v) | + |
| Requirement of acetic acid for growth | − |
| Growth on methanol | − |
| Acid formation from D-Glucose | + |
| Acetic acid production from ethanol | + |
| Cellulose formation | + |

Complete Process of Isolation of the Bacterial Strains from Fruit Residue is Described Herein Below:

For isolation of cellulose producing bacterial strains, each of the collected fruit residue was mixed with sugar and water in the ratio of 1 to 3:0.1 to 0.5:2 to 4, respectively. The mixture was then kept in a wide mouthed plastic container and covered with a piece of cloth. The container was kept at temperature of 25 to 35 degree C. for 10 days undisturbed and observed for the formation of a pellicle (mat like structure) on the top of the fruit residue mixture. The mat like structure obtained was analyzed for the presence of cellulose fibrils by calcofluor staining and electron microscopy. The cellulose producing bacteria from the pellicle was isolated after treatment of pellicle with cellulase enzyme (1 mg/ml) at 50 degree C. for 48 h. Further, the bacterial strain obtained was identified on the basis of its physico-chemical properties.

The present invention further describes an optimized economic process for the production of microbial cellulose by the said bacterial strains.

The process of the invention involves the following steps:
Isolation of microbial cellulose producer/s was carried using different fruit residues viz. pineapple, apple, orange, pomegranate, sweet lime and mixed fruit.
A newer and potent MC producing bacterial species, identified as *Gluconacetobacter oboediens* was obtained from mixed fruit residue.
Process optimization for maximum microbial cellulose production by the said bacterium was carried out by two approaches: 1) One variable at a time approach, 2) Response surface methodology.
Different physiological and nutritional factors were optimized in order to maximize microbial cellulose production viz. agitation, production medium, pH, temperature, inoculum age, inoculum size, incubation period, carbon and nitrogen sources, metal ions, vitamins etc.
Production of microbial cellulose was carried out under shaking and static culture conditions in Hestrin-Schramm medium (containing (%): glucose, 2.0%, peptone, 0.5%, yeast extract, 0.5%, citric acid, 0.115% and disodium hydrogen phosphate, 0.27%). Static culture was found to be more suitable for production of MC giving higher yield (0.45 to 0.75 g/l) as compared to shaking culture (0.08-0.18 g/l).

Microbial cellulose production was carried out using eight different production media. Results showed that CSL-Fructose medium (containing per liter: Corn Steep Liquor 40 ml, Fructose, 70 g, $K_2HPO_4$, 1 g $MgSO_4.7H_2O$, 0.25 g, $(NH_4)_2SO_4$, 5.0 g, $FeSO4.7H_2O$, 3.6 mg, $CaCl_2.2H_2O$, 14.7 mg, $NaMoO_4.2H_2O$, 2.42 mg; $ZnSO_4.7H_2O$, 1.73 mg, $MnSO_4.5H_2O$, 1.39 mg; $CuSO_45H_2O$, 0.05 mg Vitamin solution, 10 ml. Vitamin solution consisted of (per 1 L): Inositol, 200 mg; Nicotinic acid, 40 mg: Pyridoxine hydrochloride, 40 mg; Thiamine hydrochloride, 40 mg; Calcium pantothenate, 20 mg, Riboflavin, 20 mg, Folic acid, 0.2 mg; D-biotin, 0.2 mg), supported maximum microbial cellulose production, yielding 1.43 to 2.1 g/l microbial cellulose. Thus, this medium was selected for further optimization studies. Hereinafter, CSL-Fructose medium is also referred to as the production medium.

| Table depicting the yield of Microbial cellulose in different production media ||
|---|---|
| Production medium | MC (g/l) |
| Hestrin-Schramm medium | 0.87 |
| CSL-Fructose medium | 1.43-2.1 |
| Y3-3 medium | 0.9 |
| Generic medium | 0.45 |
| Defined medium | 0.41 |
| Coconut water medium | 1.1 |
| Pineapple juice medium | 1.3 |
| Improved medium | 0.56 |

Production of microbial cellulose by MTCC 5610 was carried out at different pH ranging from 2 to 12 adjusted with different buffers. pH in the range from 3 to 8 was found to be optimum for maximum production yielding 1.9 to 2.5 g/l microbial cellulose.

| Table depicting the Effect of pH on microbial cellulose production ||
|---|---|
| pH | MC (g/l) |
| 2 | nil |
| 3 | 1.90 |
| 4 | 2.51 |
| 5 | 2.32 |
| 6 | 2.10 |
| 7 | 2.03 |
| 8 | 1.97 |
| 9 | 1.25 |
| 10 | 0.94 |
| 11 | 0.23 |
| 12 | nil |

The bacterium MTCC 5610 was grown at temperature ranging from 10 to 45 degree C. Maximum microbial cellulose production [2.1 to 2.52 g/l] was obtained at temperature ranging from 25 to 35 degree C.

| Table depicting the Effect of temperature on microbial cellulose production ||
|---|---|
| Temperature | MC (g/l) |
| 10 | 0.08 |
| 15 | 0.31 |

-continued

Table depicting the Effect of temperature on microbial cellulose production

| Temperature | MC (g/l) |
|---|---|
| 20 | 1.1 |
| 25 | 2.44 |
| 30 | 2.52 |
| 35 | 2.14 |
| 40 | 0.94 |
| 45 | nil |

The microbial cellulose production by MTCC 5610 was carried out for different time periods under the conditions optimized so far. It was observed that the maximum microbial cellulose production (2.3 to 4.1 µl was obtained after 4 to 10 days of incubation period.

In the present invention, pieces of microbial cellulose mat containing *Gluconacetobacter oboediens* MTCC 5610 were used as inoculum. Inoculum age and size were optimized for microbial cellulose production. Inoculum of 1 to 5 days with a size of 5 to 12 mat pieces of 10×12 mm per liter was found to be optimum for maximum cellulose production (3.2 to 6.7 g/l).

Further, different nutritional factors viz., carbon and nitrogen sources, metal ions, vitamins etc. were optimized for maximizing microbial cellulose yield. Different carbon sources (monosaccharides and disaccharides) were used for microbial cellulose production and sucrose was found to be best and cheapest carbon source as compared to fructose (control) producing maximum microbial cellulose (6.5 to 7.2 g/l).

In order to make the production medium more cost effective, three different low cost carbon sources were evaluated for microbial cellulose production, viz. jaggery, cane molasses and table sugar. Among these, table sugar was found to a promising carbon source giving yield equivalent to sucrose. Table sugar is 15-20 times cheaper as compared to sucrose. Thus, the selection of table sugar as the carbon source resulted in an economic medium for microbial cellulose production. The production of microbial cellulose was carried out at different concentrations of table sugar ranging from 0.1 to 20%. Maximum production was obtained at 1.0 to 10.0% concentration of table sugar.

Microbial cellulose production was carried out in the presence of different organic and inorganic nitrogen sources. Corn steep liquor, an agro waste, was found to the best nitrogen source supporting maximum microbial cellulose production. Ammonium sulphate supported microbial cellulose production as an additive. Different concentrations of corn steep liquor ranging from 0.5 to 8.0% were used for producing microbial cellulose. Corn steep liquor at a concentration of 1.0 to 5.0% was found to be optimum for microbial cellulose production yielding 7.1 to 8.7 g/l microbial cellulose.

The basal production medium optimized so far contains a number of metal ions (metal salts) in traces. The effect of these metal ions was evaluated by carrying out microbial cellulose production in the absence and presence of these salts. It was observed that the microbial cellulose production was equal both in the absence and presence of these metal ions. Thus, all these metal salts were omitted from the production medium. This made the production medium more simple and economic. However, it was observed that the other two metal salts i.e. magnesium sulphate and dipotassium hydrogen phosphate significantly affected microbial cellulose production. The production of microbial cellulose decreased in the absence of these two salts.

The basal production medium optimized so far also contained different vitamins. The effect of these vitamins was evaluated on the production medium in the similar manner as for metal ions. The microbial cellulose production was found to be equivalent in the absence and presence of these vitamins. Thus, the vitamins were also omitted from the production medium. This made the cellulose production medium much more simple and economic.

The microbial cellulose production was further optimized by a statistical approach, Response Surface Methodology to enhance the productivity. Results show that the interaction of the most influential parameters (CSL, sugar and inoculum size) obtained after one variable at a time approach resulted in a maximum yield of 12.0 to 16.0 g/l of microbial cellulose after a period of 4 to 10 days of incubation at sugar: 1.0-8.0 (% w/v); CSL: 1.0-5.0 (% v/v) and inoculum size, 1 to 8 (mat pieces/L), whereas the maximum yield by response surface methodology was 18.0 to 20.0 g/l.

The microbial cellulose mats produced were processed and purified by alkali and acid treatment. The mats were further bleached to remove the remaining colour of the medium. The mats were finally washed with water and dried. The microbial cellulose mats were dried by freeze drying and air drying. Freeze dying provides a white paper like sheet of microbial cellulose. This method of drying is quite costly as it consumes a lot of electricity. Thus, in order to make the drying process cost effective the microbial cellulose mats were air dried using a novel, simple and economic method. The mats were dried on a wooden plank and a porous fabric at a temperature of 30 to 40 degree C. It was observed that air dying of microbial cellulose provides a transparent sheet of microbial cellulose.

Scale up of microbial cellulose production was carried out upto 5 liters in trays. It was observed that the production of microbial cellulose was successfully scaled upto 5 liters yielding 60-80 g of microbial cellulose. This proves that microbial cellulose can be successfully produced to any amount and size.

Further, the microbial cellulose was produced in different shapes, viz. gloves and vessels. This explains one of the most important properties of microbial cellulose that it can be molded in any shape, which makes microbial cellulose an important and versatile material for different medical applications.

Thus, it can be inferred that the microbial cellulose produced by the novel isolated strain of *Gluconacetobacter oboediens* MTCC 5610 has immense importance in different sectors, especially in the medical field. The important applications of microbial cellulose are presented in the following table:

| INDUSTRIAL SECTORS | APPLICATIONS |
|---|---|
| Health care | 1. Wound care dressings |
| | 2. Drug delivery agent, either oral or dermal |
| | 3. Artificial skin substrate |
| | 4. Component of dental and arterial implants |
| Cosmetics and Beauty | 1. Skin creams |
| | 2. Astringents |
| | 3. Base for artificial nails |
| | 4. Thickener and strengthener for fingernail polish |
| | 5. Tonics |
| | 6. Nail conditioners |
| Food | 1. Desserts (Nata de Coco, low calorie ice creams chips, snacks, candies) |

-continued

| INDUSTRIAL SECTORS | APPLICATIONS |
|---|---|
| | 2. Thickners (ice cream and salad dressing) |
| | 3. Base for weight reduction |
| | 4. Sausage and meat casings |
| | 5. Serum cholesterol reduction |
| | 6. Kombucha elixir or Manchurian tea |
| Cellulose derived products | Production of cellophane, carboxymethyl cellulose and cellulose acetate |
| Clothing and shoe | 1. Artificial leather products |
| | 2. One piece textiles |
| | 3. Highly adsorptive materials |
| Petroleum and mining | 1. Mineral and oil recovery |
| | 2. Recycling of minerals and oils |
| Papers | 1. Archival document repair |
| | 2. Paper base for long lived currency |
| | 3. Specialty papers |
| | 4. Napkins |
| Forest products | 1. Artificial wood strengthener (plywood laminates) |
| | 2. Filler for paper |
| | 3. High strength containers |
| | 4. Multilayer plywood |
| | 5. Heavy duty containers |
| Audio products | Superior audio speaker diaphragms |
| Outdoor sports | 1. Disposable tents and camping gear |
| | 2. Sport clothes |
| Public utilities | 1. Water purification via ultra filters and reverse osmosis membranes |
| Babycare products | 1. Disposable recyclable diapers |
| Automotive and aircraft | 1. Car bodies |
| | 2. Airplane structural elements |
| | 3. Sealing of cracks in rocket casings |

EXAMPLES

The following examples are given by way of illustration and therefore should not be construed to limit the scope of the present invention.

Example 1: Isolation of Cellulose Producer/s from Fruit Residues

The isolation of cellulose producer/s was carried out using six different fruit residues (apple, pineapple, orange, sweet lime, pomegranate and mixed). Here, each fruit residue was mixed with sugar and water in the ratio of 1:0.2:3, respectively. The mixture was kept in a wide mouthed plastic container and covered with a piece of cloth. The container was kept at temperature of 30 degree C. for 10 days undisturbed and observed for MC production. After 10 days, it was observed that at the top of the pineapple, orange, sweetlime and mixed fruit residue mixtures, a mat like structure was deposited. This mat like structure was analyzed for the presence of cellulose fibrils by calcofluor staining and electron microscopy. The results showed that the mat like structure was composed of a network of ultrafine cellulose fibrils and it also contained rod shaped bacterial cells producing cellulose [FIGS. 1, 3 & 4].

Example 2: Screening of the Bacterial Isolates Obtained from Fruit Residues for Microbial Cellulose Production All the isolates obtained from different fruit residues were evaluated for their potential to produce microbial cellulose. These isolates were inoculated individually in 250 ml Erlenmeyer flasks containing 50 ml cellulose production medium (Hestrin-Schramm medium) containing (g/l) glucose, 20; peptone, 5; yeast extract, 5; disodium hydrogen phosphate, 2.7 and citric acid, 1.15; and incubated for 15 days at 30 degree C. under static conditions for cellulose production. A compact mat was formed on the air-liquid interface of the medium by all the isolates. The mat was removed from the medium and examined for the presence of cellulose fibrils by calcoflour staining and SEM observation [FIGS. 3 & 4]. The mat was found to be composed of cellulose fibrils. The isolate obtained from the mixed fruit residue was found to be the most potent cellulose producer producing maximum microbial cellulose (0.45 to 0.75 g/l). Further, it was identified as *Gluconacetobacter oboediens* by 16S rRNA (875 base pair) analysis. Sequence of 16S rRNA has been provided herein.

SEQ ID No. 1: 16S rRNA sequence of
*Gluconacetobacter oboediens*
TTTTTTTCCCCCCCGGAACGTCACGCGGCATCCTGATCCGCGATTACTAG

CGATTCCACCTTCATGCACTCGAGTTGCAGAGTGCAATCCGAACTGAGAC

GGCTTTTTGAGATCGGCTCGGTGTCACCACCTGGCTTCCCACTGTCACCG

CCATTGTAGCACGTGTGTAGCCCAGGACATAAGGGCCATGAGGACTTGAC

GTCATCCCCACCTTCCTCCGGCTTGTCACCGGCAGTTCCTTTAGAGTGCC

CACCCAGACGTGATGGCAACTAAAGGCGAGGGTTGCGCTCGTTGCGGGAC

TTAACCCAACATCTCACGACACGAGCTGACGACAGCCATGCAGCACCTGT

GCTGGAGGTCTCTTGCGAGAAATGCCCATCTCTGGACACGGCCTCCGCAT

GTCAAGCCCTGGTAAGGTTCTGCGCGTTGCTTCGAATTAAACCACATGCT

CCACCGCTTGTGCGGGCCCCCGTCAATTCCTTTGAGTTTCAACCTTGCGG

CCGTACTCCCCAGGCGGTGTGCTTATCGCGTTAACTACGACACTGAATGA

CAAAGTCACCCAACATCCAGCACACATCGTTTACAGCGTGGACTACCAGG

GTATCTAATCCTGTTTGCTCCCCACGCTTTCGCGCCTCAGCGTCAGTCAT

GAGCCAGGTTGCCGCCTTCGCCACCGGTGTTCTTCCCAATATCTACGAAT

TTCACCTCTACACTGGGAATTCCACAACCCTCTCTCACACTCTAGTCGCC

ACGTATCAAATGCAGCCCCCAGGTTAAGCCCGGGAATTTCACATCTGACT

GTGTCAACCGCCTACGCGCCCTTTACGCCCAGTCATTCCGAGCAACGCTT

GCCCCCTTCGTACTACAGCGCTGCGCGCGCGCACACAAAG

Example 3: Air Drying (Drying at Room Temperature) of Microbial Cellulose

The air drying method of microbial cellulose has one drawback i.e it sticks to the base on which it is kept for drying and it becomes difficult to recover it. For solving this problem, two bases were discovered and used for the air drying of the microbial cellulose mats. These were: a wooden plank and a porous fabric. The wet mats of purified microbial cellulose were placed on these two bases and left for 45 hours at a temperature of 35 degree C. After this time period, the mats were fully dried. It was observed that the mats did not sticked on the bases used and were easily recovered [FIG. 5].

The reason behind the success of these two bases is that both the materials are porous and the air passes through them, while in all the other cases where the mat sticks on the base, a vacuum is created because the bases used were not porous but rigid and do not allow any air to pass through them. Therefore, the microbial cellulose sticks on these bases and cannot be removed.

Example 4: Scale Up of Microbial Cellulose Production Up to 5 L in Static Culture in Different Tray Sizes Trays of four different sizes viz. 18×14×5 cm³, 28×23×5 cm³, 33.5×28×4.5 cm³ and 42×34×7 cm³ were used for scale up of production of microbial cellulose upto 5 L in static culture. The trays were sterilized and the sterilized production medium was poured aseptically in trays with different volumes i.e. 200, 500, 1000, 2000, 3000, 4000 and 5000 ml. These trays were inoculated with mat pieces (2 to 8 mat pieces of 10×12 mm per liter) and incubated at a temperature of 30 degree C. for 10 days under static conditions [FIG. 6].

After incubation it was observed that a compact and rigid microbial cellulose mat having considerable strength and dimension as the respective tray size and depth of the medium was produced successfully upto 5 L. The dimension of the 5 L microbial cellulose mat was 42×34×2.7 cm³ with a cellulose yield of 60 to 80 g.

Example 5: Production of Microbial Cellulose in the Shape of Gloves and Vessels In this experiment, latex gloves and silicon tubes (30 cm long) of different diameters viz. 3 and 6 mm (inner diameter) were used for producing microbial cellulose in their respective shapes. These materials were sterilized at 15 psi for 15 min. Before sterilization, both mouth ends of the silicon tubes were closed with a piece of klin wrap. Cellulose production medium was prepared and sterilized. Now, the sterilized medium was poured aseptically in the gloves (200 ml) and tubes (10-40 ml capacity). The gloves were hanged with the help of a support in a big glass container. They were incubated at a temperature of 35 degree C. for 5 days under static conditions. It was observed that the microbial cellulose was successfully produced in the shape of gloves and tubes/vessels [FIG. 7].

Advantages

The main advantages of the present invention are:
- The bacterial species used in the present invention, *Gluconacetobacter oboediens*, is a new microbial cellulose producer. The production of microbial cellulose by this species of *Gluconacetobacter* is not reported earlier. This is the first report of microbial cellulose production by this bacterial culture. Thus, the present invention relates to the production of microbial cellulose by a novel microorganism.
- The optimized production medium i.e. CSL-Fructose medium used for microbial cellulose production is simple and economic containing low cost carbon and nitrogen sources, viz. table sugar & corn steep liquor (agro waste), respectively and only few salts in traces.
- It provides an optimized, efficient and cost effective process for the production of high titers of microbial cellulose and further, its successful scale up in static culture in trays.
- All the optimization experiments of microbial cellulose production conducted in 1 liter volume have the potential to be scaled up in all sets of experiments.
- The present invention also provides a novel and economic method for air drying of microbial cellulose mats using a wooden plank and porous fabric as a base. This step is very important as after drying only, the final dry weight of the microbial cellulose can be taken.

What is claimed is:

1. A product comprising a culture medium comprising sugar of about 1.0-8.0 (% w/v) and corn steep liquor at about 1.0 to 5.0 (% v/v) and a culture of an isolated, bacterial strain of *Gluconacetobacter oboediens* having accession number MTCC 5610, wherein the product comprises microbial cellulose of at least 12 grams/liter.

2. The product as claimed in claim 1, wherein the product comprises microbial cellulose of at least 16 grams/liter.

3. A process for the production of microbial cellulose comprising culturing an isolated bacterial strain of *Gluconacetobacter oboediens* having accession number MTCC 5610 in a culture medium containing sugar of about 1.0-8.0 (% w/v) and corn steep liquor at 1.0 to 5.0 (% v/v) for a period of 4 to 10 days, followed by recovering the cellulose.

4. A process as claimed in claim 3, wherein the sugar is table sugar.

5. A process as claimed in claim 3, wherein during the recovery step placing wet mats of purified cellulose on wooden planks or a porous fabric for air drying.

* * * * *